United States Patent [19]

Koyama et al.

[11] Patent Number: 5,827,687

[45] Date of Patent: Oct. 27, 1998

[54] PROMOTER AND METHOD OF GENE EXPRESSION USING THE SAME

[75] Inventors: Nobuto Koyama, Uji; Eiji Miyoshi, Osaka; Yoshito Ihara, Mino; Atsushi Nishikawa; Naoyuki Taniguchi, both of Toyonaka, all of Japan

[73] Assignee: Takara Shuzo Co., Ltd., Kyoto-fu, Japan

[21] Appl. No.: 672,569

[22] Filed: Jun. 28, 1996

[30] Foreign Application Priority Data

Jun. 30, 1995 [JP] Japan .................................. 7-187753
Aug. 17, 1995 [JP] Japan .................................. 7-233364

[51] Int. Cl.⁶ ...................................................... C12P 21/06
[52] U.S. Cl. .................. 435/69.1; 435/172.3; 435/320.1; 435/365; 536/241
[58] Field of Search ..................... 435/193, 69.1, 435/320.1, 172.3, 240.2, 70.1, 365; 424/94.5; 536/23.2, 350, 24.1

[56] References Cited

U.S. PATENT DOCUMENTS 5,496,731  3/1996  Xu et al. .............................. 435/320.1

FOREIGN PATENT DOCUMENTS

0585083A1  8/1993  European Pat. Off. .
0 525 083 B1  3/1994  European Pat. Off. .
0 585 083 A1  3/1994  European Pat. Off. .
6-62865  3/1994  Japan .

OTHER PUBLICATIONS

Ihara, Y et al. 1993 J. Biochemistry 113: 692–698.
Wood, K. 1995 Current Opinion in Biotechnology 6:50–58.
Barinaga, M. Science 266: 1326.
Marshall, E. Science 269:1050–1055.
Crystal, R. 1995 Science 270: 404–410.
Yoshito Ihara et al., Journal of Biochemistry, cDNA Cloning, Expression . . . , vol. 113, pp. 692–698, 1993.
Atsushi Nishikawa et al., The Journal of Biological Chemistry, Purification, cDNA Cloning . . . , vol. 267(25), pp. 18199–18204, 1992.
Kim et al., Gene 170:281–283 (1996).
Koyama et al., Eur. J. Biochem. 238:853–861 (1996).
Yang et al., Glycobiology, 4(5), pp. 703–713, 1994.

*Primary Examiner*—Nancy Degen
*Assistant Examiner*—Irem Yucel
*Attorney, Agent, or Firm*—Birch, Stewart, Kolasch & Birch, LLP

[57] ABSTRACT

An isolated DNA having a promoter activity in an animal cell; a method for expressing a useful gene using the isolated DNA; and a method for producing a protein in an animal cell using the isolated DNA. The present invention provides a method for producing a desired gene product in a large quantity in an animal cell.

14 Claims, 2 Drawing Sheets

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 1116 base pairs
        ( B ) TYPE: nucleic acid
        ( C ) STRANDEDNESS: double
        ( D ) TOPOLOGY: linear ( i i ) MOLECULE TYPE: genomic DNA ( i i i ) HYPOTHETICAL: No ( i v ) ANTI-SENSE: No ( x i ) SEQUENCE DESCRIPTION: SEQ ID NO:1:

```
GCATGCGCCA  CTACACTCAG  CTACTTTGTA  TTTTAGTAG   AGACAGGGTT  TCACCATGTT     60

GGCCAGGCTG  GTCTCGAACT  CCTGACCTTG  TGATCTGCCC  ACCTCGGCCT  CCCAAAGTGC    120

TGGGATTATA  GGCGTGAGCC  ACTGCACTGG  CCGACCTCAA  ATTTTTATGC  CTGGAGATTA    180

GTAAAGGGCA  TGGAATAATG  AAGGGGAACT  TTTATTTAT   TTTGTTTTTG  AGATAGGGTC    240

TCAGTCTGTT  GTCCAGGCTG  GGGCGCAGTG  GTGCAATCAT  GGCTCACTGC  AGCCTCAACC    300

TCGAGGTCTC  AAGTGATCCT  CCCACCTCAC  CTCAGCCTCC  TAAGTAGCTG  GGACCACAAG    360

CACATGGCAC  CACACCTGGC  ACCACACCTG  GCTAATTTTT  AAATTTTCTG  TAGAGATGGG    420

GTCTCACTAT  GTTGTCCAGC  TGGTCTCAAA  CTCCTGGGCT  CAAGTGATCC  TCCTGCCTCA    480
```

| | | | | | | |
|---|---|---|---|---|---|---|
|GCCTCTGAAG|GTGTTGGGAT|TACAGGCGTG|AGCACCACGC|CTGGCCTAAT|TTTATTCATT|540|
|AAATATGTTA|GAATTAAGTG|TTTTCCCTTG|AGACCTGTGA|GTTTTTCAGT|GAAAAATATT|600|
|CAAAAGGTTT|GTCAGTATGT|CCATAAAAAA|GAAGATAGGA|GGGGAGGGAC|AGGACCCAGG|660|
|AGGGCAGCCT|ACAGCCTGCT|CTCCCCGTTC|TGTCCTGGGG|CGGAGTCTGT|ACTGCGAGTT|720|
|GAGCTTTTCC|CAAGTCGTCA|TGTTACTCCT|GGAGCCAAGC|CTAGCAGTGC|AGCCTCACAG|780|
|TCAGGTTGGG|GTGGTCCAGC|GGAGAAGCAG|GCTGCAGAGG|GGGCAGGGTG|GTGGCCTGGG|840|
|GATCTCAGGG|AAGGGCTATG|GGAGCACGGC|GGTGTCCTCA|GTGCTGGGC|TTTCAGGGGC|900|
|CTTGGTACCG|CGAGTTGACT|CTTGGGGGCA|GGAGGTCACT|CCATGCAGGG|GCAGCAGGTG|960|
|CTGGCCACCA|CATTGTCCAG|CAAGGTGGCA|GCAGAGGCCT|CCTAGGTCCC|CTTCCTAGGA|1020|
|AAGGAGCCTG|GGCTGCCCTG|ATGAGTCTCC|TGTCTCTCTC|TCTCCCGCAG|GATGAAGATG|1080|
|AGACGCTACA|AGCTCTTTCT|CATGTTCTGT|ATGGCC| | |1116|

(2) INFORMATION FOR SEQ ID NO:2:

(i) SEQUENCE CHARACTERISTICS:
    (A) LENGTH: 817 base pairs
    (B) TYPE: nucleic acid
    (C) STRANDEDNESS: double
    (D) TOPOLOGY: linear (ii) MOLECULE TYPE: genomic DNA (iii) HYPOTHETICAL: No (iv) ANTI-SENSE: No (xi) SEQUENCE DESCRIPTION: SEQ ID NO:2:

| | | | | | | |
|---|---|---|---|---|---|---|
|CTCGAGGTCT|CAAGTGATCC|TCCCACCTCA|CCTCAGCCTC|CTAAGTAGCT|GGGACCACAA|60|
|GCACATGGCA|CCACACCTGG|CACCACACCT|GGCTAATTTT|TAAATTTTCT|GTAGAGATGG|120|
|GGTCTCACTA|TGTTGTCCAG|CTGGTCTCAA|ACTCCTGGGC|TCAAGTGATC|CTCCTGCCTC|180|
|AGCCTCTGAA|GGTGTTGGGA|TTACAGGCGT|GAGCACCACG|CCTGGCCTAA|TTTTATTCAT|240|
|TAAATATGTT|AGAATTAAGT|GTTTTCCCTT|GAGACCTGTG|AGTTTTTCAG|TGAAAAATAT|300|
|TCAAAAGGTT|TGTCAGTATG|TCCATAAAAA|AGAAGATAGG|AGGGGAGGGA|CAGGACCCAG|360|
|GAGGGCAGCC|TACAGCCTGC|TCTCCCCGTT|CTGTCCTGGG|GCGGAGTCTG|TACTGCGAGT|420|
|TGAGCTTTTC|CCAAGTCGTC|ATGTTACTCC|TGGAGCCAAG|CCTAGCAGTG|CAGCCTCACA|480|
|GTCAGGTTGG|GGTGGTCCAG|CGGAGAAGCA|GGCTGCAGAG|GGGGCAGGGT|GGTGGCCTGG|540|
|GGATCTCAGG|GAAGGGCTAT|GGGAGCACGG|CGGTGTCCTC|AGTGCTGGGG|CTTTCAGGGG|600|
|CCTTGGTACC|GCGAGTTGAC|TCTTGGGGGC|AGGAGGTCAC|TCCATGCAGG|GGCAGCAGGT|660|
|GCTGGCCACC|ACATTGTCCA|GCAAGGTGGC|AGCAGAGGCC|TCCTAGGTCC|CCTTCCTAGG|720|
|AAAGGAGCCT|GGGCTGCCCT|GATGAGTCTC|CTGTCTCTCT|CTCTCCCGCA|GGATGAAGAT|780|
|GAGACGCTAC|AAGCTCTTTC|TCATGTTCTG|TATGGCC| | |817|

(2) INFORMATION FOR SEQ ID NO:3:

(i) SEQUENCE CHARACTERISTICS:
    (A) LENGTH: 522 base pairs
    (B) TYPE: nucleic acid
    (C) STRANDEDNESS: double
    (D) TOPOLOGY: linear (ii) MOLECULE TYPE: genomic DNA (iii) HYPOTHETICAL: No -continued (iv) ANTI-SENSE: No (xi) SEQUENCE DESCRIPTION: SEQ ID NO:3:

| | | | | | | |
|---|---|---|---|---|---|---|
| AATATTCAAA | AGGTTTGTCA | GTATGTCCAT | AAAAAGAAG | ATAGGAGGGG | AGGGACAGGA | 60 |
| CCCAGGAGGG | CAGCCTACAG | CCTGCTCTCC | CCGTTCTGTC | CTGGGGCGGA | GTCTGTACTG | 120 |
| CGAGTTGAGC | TTTTCCCAAG | TCGTCATGTT | ACTCCTGGAG | CCAAGCCTAG | CAGTGCAGCC | 180 |
| TCACAGTCAG | GTTGGGGTGG | TCCAGCGGAG | AAGCAGGCTG | CAGAGGGGC | AGGGTGGTGG | 240 |
| CCTGGGGATC | TCAGGGAAGG | GCTATGGGAG | CACGGCGGTG | TCCTCAGTGC | TGGGGCTTTC | 300 |
| AGGGGCCTTG | GTACCGCGAG | TTGACTCTTG | GGGGCAGGAG | GTCACTCCAT | GCAGGGGCAG | 360 |
| CAGGTGCTGG | CCACCACATT | GTCCAGCAAG | GTGGCAGCAG | AGGCCTCCTA | GGTCCCCTTC | 420 |
| CTAGGAAAGG | AGCCTGGGCT | GCCCTGATGA | GTCTCCTGTC | TCTCTCTCTC | CCGCAGGATG | 480 |
| AAGATGAGAC | GCTACAAGCT | CTTTCTCATG | TTCTGTATGG | CC | | 522 |

(2) INFORMATION FOR SEQ ID NO:4:

(i) SEQUENCE CHARACTERISTICS:
  (A) LENGTH: 200 base pairs
  (B) TYPE: nucleic acid
  (C) STRANDEDNESS: double
  (D) TOPOLOGY: linear (ii) MOLECULE TYPE: genomic DNA (iii) HYPOTHETICAL: No (iv) ANTI-SENSE: No (xi) SEQUENCE DESCRIPTION: SEQ ID NO:4:

| | | | | | | |
|---|---|---|---|---|---|---|
| GACTCTTGGG | GGCAGGAGGT | CACTCCATGC | AGGGGCAGCA | GGTGCTGGCC | ACCACATTGT | 60 |
| CCAGCAAGGT | GGCAGCAGAG | GCCTCCTAGG | TCCCCTTCCT | AGGAAAGGAG | CCTGGGCTGC | 120 |
| CCTGATGAGT | CTCCTGTCTC | TCTCTCTCCC | GCAGGATGAA | GATGAGACGC | TACAAGCTCT | 180 |
| TTCTCATGTT | CTGTATGGCC | | | | | 200 |

PROMOTER AND METHOD OF GENE EXPRESSION USING THE SAME

BACKGROUND OF THE INVENTION

1. Field of the Invention

The present invention relates to a novel promoter and to a method for expressing a gene using the novel promoter. Specifically, the invention relates to a DNA comprising the novel promoter which is capable of functioning in animal cells and to a method for producing a protein using a vector into which a DNA obtained by ligating a useful gene downstream of the promoter is inserted. The present invention also relates to a method for expressing a useful gene, comprising ligating the useful gene downstream of the promoter, and introducing the resulting DNA or a vector carrying the resulting DNA into an animal cell.

2. Discussion of the Related Art

When a microbial host, such as *Escherichia coli, Bacillus subtilis* or yeast, is used to produce a useful gene product of animal origin by gene engineering technology, gene expression is often hampered. Obtaining the desired activity is often hampered due to incorrect conformation, incorrect post-translational modification, etc. of the gene product protein. To cope with this problem, animal cells are often used as hosts, in which case promoter selection significantly affects expression efficiency. Conventional promoters for animal cells in common use include the SV40 promoter, cytomegalovirus promoter and actin promoter.

When a large amount of a useful gene product is to be produced using an animal cell as the host, the conventionally used promoters for animal cells are not satisfactory in terms of transcription activity. Hence, the development of more potent promoter has been in demand.

Accordingly, an object of the present invention is to provide a DNA with high promoter activity as a promoter for animal cells. Another object of the present invention is to provide a method for expressing a useful gene using the promoter.

SUMMARY OF THE INVENTION

In order to achieve the above objects, the present inventors conducted intensive studies in an effort to obtain a promoter with a high transcription efficiency. As a result, the present inventors found that a potent promoter exists upstream the human N-acetylglucosaminyltransferase III (human GnT-III) gene.

The present inventors further determined the nucleotide sequence of the DNA comprising the promoter, ligated the DNA upstream the Photinus luciferase gene, and expressed the gene. As a result, they have confirmed that the promoter has much higher activity than the conventional promoters for animal cells. Based upon these findings, the present invention has been completed.

In one embodiment, the present invention relates to an isolated DNA having a sequence selected from the group consisting of:

(a) a DNA sequence comprising a sequence of SEQ ID NO:1, or a fragment thereof;
(b) a DNA sequence comprising a sequence of SEQ ID NO:2, or a fragment thereof;
(c) a DNA sequence comprising a sequence of SEQ ID NO:3, or a fragment thereof;
(d) a DNA sequence comprising a sequence of SEQ ID NO:4, or a fragment thereof; and
(e) a DNA sequence capable of hybridizing to any one of (a) to (d) above, wherein said isolated DNA has a promoter activity in an animal cell.

In another embodiment, the invention relates to a recombinant DNA which comprises the above isolated DNA and a useful gene operably linked thereto, to a vector which comprises the recombinant DNA, to an animal cell to which the recombinant DNA or the vector is introduced, and to an animal having the animal cell.

In another embodiment, the invention relates to a method for producing a protein and to a method for expressing a useful gene, using the recombinant DNA of the present invention.

DETAILED DESCRIPTION OF THE INVENTION

Figure 1:
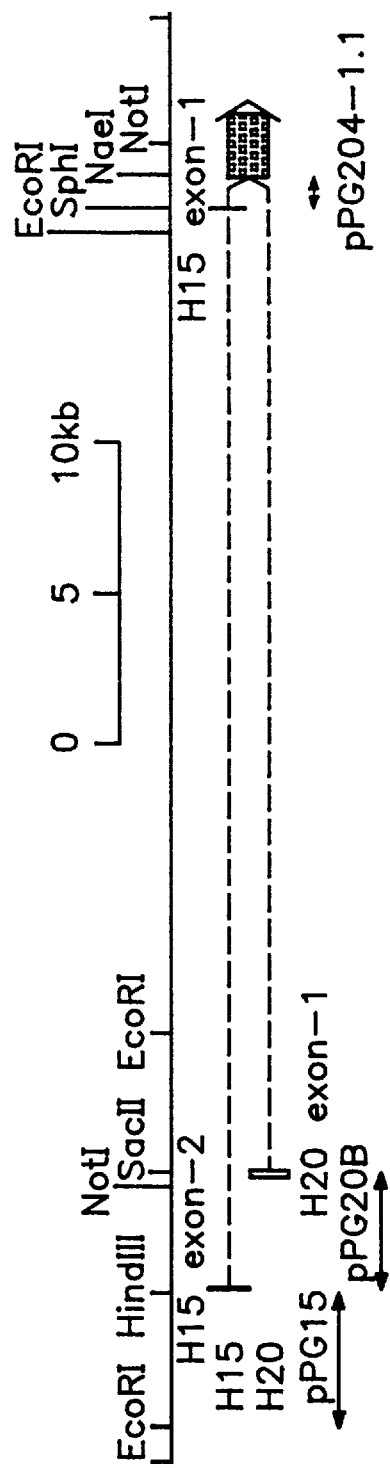
FIG. 1 indicates the relation between the DNA comprising the promoter of the present invention (pPG204-1.1) and the cDNA of human GnT-III gene.

The term "promoter" as used herein is intended to include the TATA box or a similar region, which is located 20 to 30 base pairs upstream of the replication initiation point (+1) and which functions to induce RNA polymerase to initiate transcription at the right position, but is not limited to portions near this region. In addition to this region, another necessary region for association of a protein other than RNA polymerase may be present for regulation of expression. The term "promoter region" as used herein is defined as a region containing a promoter as defined herein.

The term "promoter activity" as used herein means that when a useful gene is ligated downstream of a promoter in a manner such that the gene is expressible, and introduced to a host (animal cell), the host shows the capability and function of producing a product of the useful gene in or out of the host.

In general, promoter activity, or presence or absence or potency of a particular promoter, is determined by ligating a gene encoding a readily quantifiable protein (reporter gene) downstream of the promoter in a manner such that the gene is expressible, introducing the gene to a host, and measuring the amount of protein expressed. When a useful gene is ligated downstream of a promoter in a manner such that the gene is expressible, and introduced to a host, and when the expression product of the useful gene is confirmed in or out of the host, the promoter can be said to have promoter activity in the host to which it is introduced.

The term "animal cell" as used herein is intended to include, but is not limited to, human cells, as long as the promoter of the present invention shows promoter activity in the animal cell. Such animal cells include cells of non-human mammals (e.g., mice, rats, rabbits, goat, pigs, bovines, horses, dogs, monkeys, and chimpanzees), birds (e.g., chickens, turkeys, quails, ducks, and wild ducks), reptiles (e.g., snakes, crocodiles, and turtles), amphibians (e.g., frogs, salamanders, and newts) and fishes (e.g., horse mackerels, mackerels, sea basses, sea breams, groupers, yellow tails, tunas, salmon, trout, carp, ayu, eels, flatfishes, sharks, rays, and sturgeons).

The term "useful gene" as used herein is intended to include genes encoding a protein expressible in animal cells, antisense DNA or antisense RNA of genes of animal cell origin, decoys, e.g., a DNA sequence containing a gene encoding a binding protein of a transcription factor of animal cell origin or a DNA sequence encoding the transcription factor binding site and a similar sequence, and ribozymes which cleave mRNA of animal cell origin.

Genes encoding a protein expressible in animal cells include, but are not limited to, genes of animal origin. As long as they are expressible in animal cells, genes derived from microorganisms, such as bacteria, yeasts, actinomycetes, molds, ascomycotina and basidiomycetes, and those derived from non-microbial organisms, such as plants and insects, are also included in the useful genes mentioned herein.

The term "decoy" as used herein is intended to indicate a DNA sequence having a gene encoding a binding protein of a transcription factor of animal cell origin or a DNA sequence having a sequence of the transcription factor binding site or a similar sequence, the DNA sequence of "decoy" being capable of suppressing the action of the transcription factor when introduced to a cell as "lure".

The term "ribozyme" as used herein is defined as an enzyme which cleaves the mRNA of a particular protein to inhibit the translation of the protein. A ribozyme can be designed from the gene sequence encoding a particular protein. For example, a hammer head type ribozyme can be prepared by the method described in the FEBS Letter, 228, 228–230 (1988). In addition to hammer head type ribozymes, ribozymes of the hairpin type, delta type or other types are included in the scope of the ribozymes mentioned herein, as long as they cleave the mRNA of a particular protein to inhibit the translation of the protein.

By operably linking a useful gene downstream of the DNA fragment possessing promoter activity of the present invention, the expression of the useful gene can be enhanced. The expression of the useful gene takes place in animal cells where the DNA fragment possessing promoter activity of the present invention may be introduced by means of a vector or without using a vector. As a vector, a plasmid vector or a virus vector is preferably used. In a case without using a vector, the DNA fragment can be introduced directly by the method described in Virology, 52, 456 (1973), Molecular and Cellular Biology, 7, 2745 (1987), Journal of the National Cancer Institute, 41, 351 (1968), EMBO Journal, 1, 841(1982), and BioTechniques, 6, 682 (1988). The animal cells harboring the DNA fragment of the invention and animals having such animal cells are also included in the scope of the invention. The useful genes of which expression can be enhanced by the present invention include a DNA encoding a protein, antisense DNA, antisense RNA, a polynucleotide encoding a decoy, a nucleotide sequence that can function as a decoy, and a ribozyme. The present invention also discloses the method for producing a desired protein and the method for expressing a useful gene by use of the DNA fragment possessing promoter activity of the present invention.

The DNA of the present invention possesses promoter activity for animal cells and contains the entire or partial portion of the DNA sequence of SEQ ID NO:1 in the sequence listing. In other words, the DNA fragment of the present invention is a DNA fragment containing a novel promoter and, as long as it contains said promoter, it may be any fragment of the DNA sequence of SEQ ID NO:1 or may be any fragment containing a portion of the DNA sequence of SEQ ID NO:1. Such DNA fragments include, but are not limited to, the DNA fragments of SEQ ID NO:2, SEQ ID NO:3 and SEQ ID NO:4, and DNA fragments comprising a portion of the DNA fragment of SEQ ID NO:2 or SEQ ID NO:3 and DNA fragments containing the entire or partial portion of the DNA sequence of SEQ ID NO:4. DNA fragments capable of hybridizing to these DNA fragments, and possessing promoter activity in animal cells, are also included in the scope of the DNA fragment of the present invention.

The promoter of the present invention for animal cells was discovered as follows:

The human GnT-III gene, isolated from a fetal hepatic cDNA library and genomic cosmid library by Ihara et al. [Journal of Biochemistry, 113, 692–698 (1993)], was used for the present invention. Of the cDNA clones encoding the human GnT-III gene, H15 and H20 (Japanese Patent Laid-Open No. 6-62865) each contain a 5' non-translational region, and the DNA sequences of the two 5' non-translational regions differ from each other except for the 8 base pairs upstream of the expected initiation codon. Two cosmids, Hug3 and Hug5, have been obtained as genomic clones, of which Hug3 contains the coding region for the GnT-III gene and about 35 kb region upstream of it.

With this in mind, Southern hybridization, DNA sequencing, etc. of the Hug3 cosmid clone were conducted with the 5' non-translational regions of H15 and H20 as probes, demonstrating that H15 has exons at about 29 kb (H15 exon-2) and 1 kb (H15 exon-1) upstream of the initiation codon, and that H20 has an exon at about 26 kb (H20 exon-1) upstream of the initiation codon. Also conducted was 5'-rapid amplification of cDNA end (RACE) with human brain mRNA as a template using a primer specific to the GnT-III gene, demonstrating the presence of mRNA without splicing at a position 7 base pairs upstream the initiation codon, where splicing occurs in H15 and H20. The cDNA obtained from this mRNA is designated as H204.

These findings demonstrate that there are at least three human GnT-III gene transcription products. Since the promoters involved in the transcription of H15, H20 and H204 are assumed to be present upstream of the H15 exon-2, upstream of the H20 exon-1 and upstream of the expected translation initiation point on the genome, respectively, the promoter activity of DNA fragment containing these regions in COS1 cells was determined with the Photinus luciferase gene as a reporter gene. As shown in FIG. 1 (boxes are exon portions; dotted lines are intron portions), no promoter activity was detected in the about 3 kb fragment (plasmid containing this fragment designated as pPG20B) upstream H20 from the HindIII site in H15 exon-2 to the SacII site in H20 exon-1. However, promoter activity was detected in the about 3 kb fragments (plasmid containing this fragment designated as pPG15) from the EcoRI site upstream of H15 to the HindIII site in H15 exon-2, and in the about 1.1 kb fragment (plasmid containing this fragment designated as pPG204-1.1) from the SphI site upstream of the coding region to the NaeI site in the coding region, i.e., the fragment containing H204; the latter found to be about 10 times as potent as the former and about 1.5 times as potent as the SV40 promoter.

Moreover, this 1.1 kb fragment contains an XhoI site at about 0.8 kb from the NaeI site, an SspI site at about 0.5 kb, and an HincII site at 0.2 kb; when pPG204-1.1 is digested with any one of these restriction enzymes in combination with BamHI, a restriction enzyme having a cleavage site at the multiple cloning site of the vector, a 0.8 kb fragment (fragment A), a 0.5 kb fragment (fragment B) and a 0.2 kb fragment (fragment C), which contain the GnT-III initiation codon, can be cut out. These fragments were found to be 2–3 times as potent as the above-mentioned 1.1 kb fragment and 3–5 times as potent as the SV40 promoter in terms of promoter activity. The present inventors thus demonstrated that the DNA fragments containing an about 0.2–1 kb portion upstream the human GnT-III gene-coding region possess potent promoter activity. The inventors made further investigation based on this finding, and developed the present invention. The method of obtaining the DNA fragment of the present invention is hereinafter described in detail.

(1) Nucleotide sequence of DNA fragment possessing promoter activity in animal cells A genomic cosmid clone containing an upstream portion of the human GnT-III gene, e.g., the cosmid clone Hug3 of Ihara et al., was cleaved with restriction enzymes SphI and NaeI (both produced by Takara Shuzo); a 1.1 kb DNA fragment containing a region immediately upstream of the coding region for GnT-III is isolated. This DNA fragment has the nucleotide sequence of SEQ ID NO:1. This fragment is subcloned into a plasmid vector, e.g., pUC19 (produced by Takara Shuzo), to facilitate its use for ligation with a useful gene and other purposes.

The nucleotide sequence of the subcloned 1.1 kb SphI-NaeI fragment (pHug5'-204) can be determined by, for example, the dideoxy method [Proceedings of the National Academy of Sciences of the USA, 74, 5463 (1977)]. It is usually difficult to determine the nucleotide sequence of a 1.1 kb DNA fragment in a single reaction; for this purpose, some methods are available, including the method in which the fragment is further digested with appropriate restriction enzymes and subcloned, followed by dideoxy reaction, the method in which a series of deletion plasmids are prepared using exonuclease III, followed by dideoxy reaction, and the method in which primers are sequentially synthesized on the basis of known nucleotide sequences, followed by dideoxy reaction. In the present invention, the fragment was further digested with restriction enzymes BstXI, XhoI, SspI, KpnI and HincII (restriction enzyme map for the pHug5'-204 inserts is shown in FIG. 2), subcloned, and subjected to dideoxy reaction, to determine the nucleotide sequence of pHug5'-204 as shown in SEQ ID NO:1 of the sequence listing.

Figure 2:
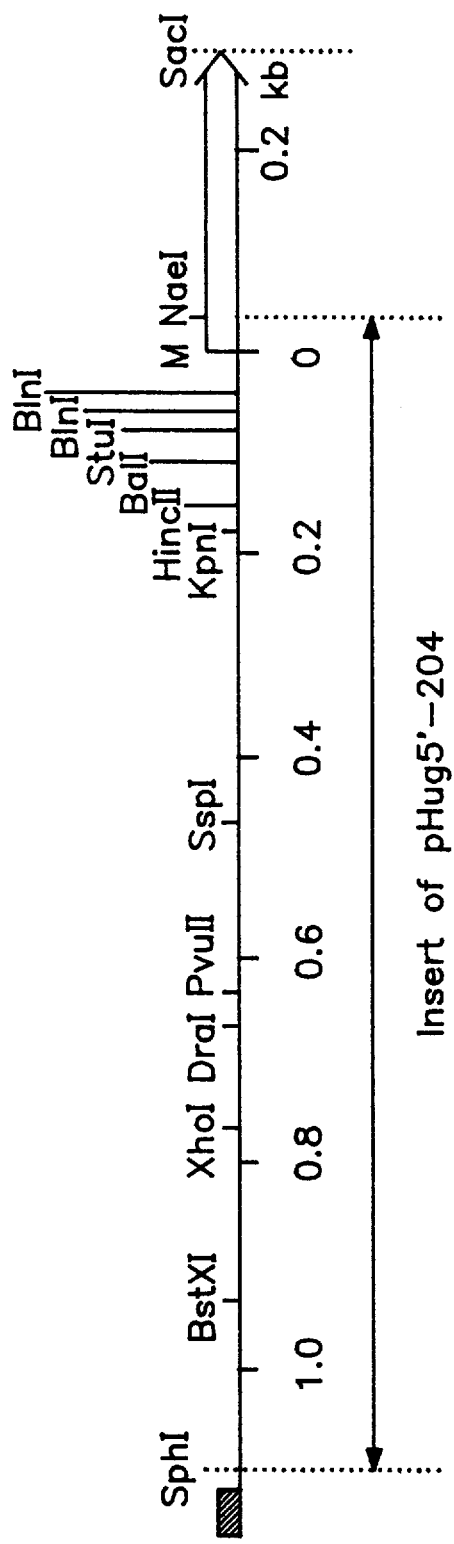
FIG. 2 is a restriction enzyme map of the insert of pHug5'-204.

As shown in FIG. 2, this 1.1 kb fragment contains an XhoI site at about 0.8 kb from the NaeI site, an SspI site at about 0.5 kb and an HincII site at 0.2 kb. When pHug5'-204 is digested with any one of these restriction enzymes in combination with BamHI, a restriction enzyme having a cleavage site at the multiple cloning site of the vector, the 0.8 kb fragment (fragment A) of SEQ ID NO:2 in the sequence listing, the 0.5 kb fragment (fragment B) of SEQ ID NO:3 and the 0.2 kb fragment (fragment C) of SEQ ID NO:4, all containing the GnT-III initiation codon, can be cut out.

(2) Preparation of DNA fragment containing the promoter of the present invention The easiest approach to the preparation of a DNA fragment containing the promoter of the present invention is to cut out it from the above-described cosmid or plasmid by digestion with restriction enzymes SphI and NaeI (both produced by Takara Shuzo), with further digestion with such restriction enzymes as XhoI, SspI and HincII as necessary. Other useful methods include digestion with other restriction enzymes, ultrasonication, chemical synthesis by the phosphoramidite method, and the method using polymerase chain reaction. For example, the desired DNA fragment can be easily prepared by the polymerase chain reaction method using an appropriate primer prepared from the DNA sequence of SEQ ID NO:1, for instance.

By hybridization using the nucleotide sequence of the promoter of the present invention, the promoter of the present invention can also be obtained from a gene derived from another cell. In this case, the following method, for example, is applicable. First, chromosomal DNA obtained from another cellular gene source is ligated to a plasmid, phage vector, or the like, by a conventional method, and introduced to a host, to prepare a library. The library is then cultured on plates; the resulting colonies or plaques are transferred onto a nitrocellulose or nylon membrane, followed by denaturation, to immobilize the DNA onto the membrane. This membrane is then incubated in a solution containing a probe, previously labeled with $^{32}P$, etc. (useful probes include the DNA fragment of SEQ ID NO:1 in the sequence listing, and portions thereof, such as fragment A (SEQ ID NO:2), fragment B (SEQ ID NO:3) and fragment C (SEQ ID NO:4)) to form a hybrid between the DNA on the membrane and the probe.

For example, the DNA-immobilized membrane is hybridized with the probe at 65° C. for 20 hours in a solution containing 6×SSC, 1% sodium dodecyl sulfate (SDS), 100 μg/ml salmon sperm DNA and 5×Denhardt's. After completion of the hybridization, non-specific adsorption is washed away, followed by autoradiography etc., to identify clones which has formed a hybrid with the probe. This procedure is repeated until a single clone has formed the hybrid. The thus-obtained single clone has the desired promoter inserted therein.

The nucleotide sequence of the obtained gene is determined by, for example, the method described below to prove the identity of the gene as the desired promoter. Nucleotide sequencing of clones obtained by hybridization is achieved as mentioned below, when the recombinant is *Escherichia coli*: the recombinant is cultured in test tubes, etc.; the plasmid is extracted and cleaved with restriction enzymes; the insert is taken out and subcloned into the M13 phage vector, etc., followed by nucleotide sequencing by the dideoxy method. When the recombinant is a phage, basically the same procedures can be followed to achieve nucleotide sequencing. These basic operations from cultivation to nucleotide sequencing can be conducted as described in, for example, Molecular Cloning: A Laboratory Manual, 2nd edition, edited by T. Maniatis et al., Chapter 1, pp. 90–104, published by Cold Spring Harbor Laboratory, 1989.

The identity of the obtained gene as the desired promoter can be estimated on the basis of the homology of the determined nucleotide sequence to the nucleotide sequence of the promoter of the present invention. When the obtained gene is not assumed to contain the entire promoter, the nucleotide sequence of the entire promoter hybridizing to the promoter of the present invention can be determined by preparing a synthetic DNA primer on the basis of the obtained gene, amplifying the lacked region by PCR, or screening a DNA library or cDNA library using a fragment of the obtained gene as a probe.

The method of the present invention for expressing a useful gene is characterized in that the useful gene is ligated downstream of the promoter of the present invention in a manner such that the gene is expressible; thus-prepared DNA fragment is introduced to an animal cell; and the resulting cell is cultured. To ligate the desired useful gene downstream the DNA fragment prepared as above, which contains the promoter of the present invention in a manner such that the gene is expressible, DNA ligase and the homopolymer method can be used. When DNA ligase is used for ligation of two DNA fragments sharing the same restriction enzyme site, ligation is achieved by digesting them with the appropriate restriction enzyme, mixing them together in the reaction buffer described in Molecular Cloning: A Laboratory Manual, 2nd edition, edited by T. Maniatis et al., Chapter 1, p. 62, published by Cold Spring Harbor Laboratory, 1989, and adding DNA ligase. Alternatively, when the two DNA fragments do not share the same restriction enzyme site, they are ligated together by blunting their ends using T4 DNA polymerase (produced by Takara Shuzo) and treating them with DNA ligase as described above. When the homopolymer method is used, a poly-G chain is added to the 3' terminal of the vector, previously linearized with restriction enzyme, using terminal deoxyribonucleotidyl transferase and dGTP; to the 3' terminal of the insert DNA, a poly-C chain is added in the same manner; these poly-G and poly-C chains are annealed together and introduced to *Escherichia coli* by, for example, the calcium chloride method [Proceedings of the National Academy of Sciences of the USA, 75, 3727 (1978)].

Examples of desired useful genes for the present invention include, but are not limited to, the interleukin 1 through 12 genes, interferon α, β and γ genes, tumor necrosis factor gene, colony-stimulating factor gene, erythropoietin gene, transforming growth factor -β gene, immunoglobulin gene, tissue plasminogen activator gene, urokinase gene and Photinus luciferase gene.

The thus-obtained DNA fragment, resulting from ligation of the DNA fragment of the present invention and a useful gene, can be inserted to an appropriate vector for animal cells to yield a plasmid for gene expression. Such vectors include pTM [Nucleic Acids Research, 10, 6715 (1982)], cos202 [The EMBO Journal, 6, 355 (1987)], p91203(B) [Science, 228, 810 (1985)] and BCMGSNeo [Journal of Experimental Medicine, 172, 969 (1990)].

The obtained plasmid for gene expression can be introduced to an appropriate host cell by conventional methods, such as the calcium phosphate method [Molecular and Cellular Biology, 7, 2745 (1987)], the electroporation method [Proceedings of the National Academy of Sciences of the USA, 81, 7161 (1984)], the DEAE-dextran method [Methods in Nucleic Acids Research, p. 283, edited by Karam, J. D. et al., published by CRC Press, 1991] and the liposome method [BioTechniques, 6, 682 (1989)]. Such host cells include COS1 cells, HELA cells, CHO-21 cells and BHK-21 cells. By culturing the obtained transformant cells in an appropriate medium, the desired useful gene product can be efficiently produced.

By use of the DNA fragment of the present invention as a promoter, a desired useful gene product can be expressed in a large quantity in an animal cell.

EXAMPLES

The following examples illustrate the present invention but are not intended to limit the invention in any manner.

Example 1

The cosmid clone Hug3, which incorporates a genome region containing the GnT-III gene reported by Ihara et al. [Journal of Biochemistry, 113, 692 (1993)], was digested with restriction enzymes SphI and NaeI (both produced by Takara Shuzo) and subjected to agarose gel electrophoresis. A 1.1 kb fragment was cut out from the gel, followed by DNA recovery using the EASYTRAP™ (produced by Takara Shuzo). This DNA fragment was ligated to pUC19, previously digested with SphI and HincII, by means of T4 DNA ligase, after which it was introduced to *Escherichia coli* XL1-Blue by the calcium chloride method. The resulting ampicillin-resistant colonies were picked up and cultured; a plasmid was prepared from the cultured cells by the alkali method. At the multiple cloning site of pUC19, HindIII, SphI, HincII and BamHI sites were mutually closely arranged in this order. The plasmid was double digested with BamHI and HindIII and subjected to agarose gel electrophoresis; the plasmid was found to contain a 1.1 kb HindIII-BamHI fragment (the nucleotide sequence of this fragment was identified as the sequence of SEQ ID NO:1), and designated as pHug5'-204. *Escherichia coli* XL1-Blue was transformed with this plasmid to yield the transformant *Escherichia coli* XL1-Blue/pHug5'-204 (deposited under FERM BP-5532 at the National Institute of Bioscience and Human-Technology, Agency of Industrial Science and Technology).

pHug5'-204 was then digested with BamHI and HindIII; the resulting 1.1 kb fragment was recovered from the agarose gel using the EASYTRAP™, followed by terminal blunting in the presence of dATP, dGTP, dCTP and dTTP using T4-DNA polymerase (produced by Takara Shuzo). Separately, an enhancer vector (produced by Toyo Ink) as a promoter-lacked plasmid containing the Photinus luciferase gene, SV40 enhancer, *Escherichia coli* replication initiation point and ampicillin resistance gene, was digested at the SmaI site immediately upstream the Photinus luciferase gene and ligated to the previously recovered 1.1 kb fragment using T4-DNA ligase, after which the ligation product was introduced to *Escherichia coli* XL1-Blue by the calcium chloride method.

To determine the orientation of the 1.1 kb fragment, a plasmid was prepared from the ampicillin-resistant bacterium, digested with XhoI, and subjected to agarose gel electrophoresis. Judging from the restriction enzyme map, it was expected that a 0.8 kb fragment will be found if the 1.1 kb fragment is inserted in the same orientation as that of the Photinus luciferase gene, and that a 0.3 kb fragment will be found if the 1.1 kb fragment is inserted in the reverse orientation. With this in mind, a plasmid harboring a 0.8 kb XhoI fragment was selected to yield pPG204-1.1.

To a 2-liter conical flask containing an LB medium [1% Bactotrypton, 0.5% Bactoyeast extract (both produced by DIFCO), 0.5% NaCl] containing 100 μg/ml ampicillin, the *Escherichia coli* harboring pPG204-1.1 was inoculated, followed by overnight shaking culture at 37° C., after which the plasmid was prepared by the cesium chloride equilibration density gradient centrifugation method described in Molecular and Cellular Biology, 7, 2745 (1987). pPG204-1.1, 20 μg per 10 cm petri dish, was transfected to COS1 cells (ATCC CRL 1650) by the calcium phosphate method described in Molecular and Cellular Biology, 7, 2745 (1987).

The luciferase activity of the transfected COS1 cells was determined using a PicaGene™kit (produced by Toyo Ink) as directed in the instruction manual for the kit. Forty-eight hours after the transfection, the cells were suspended in 0.7 ml of the cell-lysing solution included in the kit; 20 μl of the supernatant and 100 μl of a luminescence substrate were mixed together, after which luminescence intensity was immediately determined using a liquid scintillation counter. For positive control, the cells were transfected with the control vector (SV40 promoter) included in the kit; for negative control, the cells were transfected with the enhancer vector.

As a result, pPG204-1.1, incorporating the DNA fragment of the present invention, was found to be much more potent than the SV40 promoter in terms of promoter activity.

| | Relative luminescence intensity (%) |
|---|---|
| Enhancer vector | 0.4 |
| SV40 promoter | 100 |
| pPG204-1.1 | 156 |

Example 2 pHug5'-204 was digested with XhoI, followed by terminal blunting in the presence of dATP, dGTP, dCTP and dTTP using T4-DNA polymerase, after which it was further digested with BamHI and subjected to agarose gel electrophoresis, followed by recovery of a 0.8 kb fragment (fragment A) using the EASYTRAP™. Separately, pHug5'-204 was digested with SspI and BamHI, followed by recovery of a 0.5 kb fragment (fragment B) in the same manner as for fragment A. pHug5'-204 was also digested with HincII and BamHI, followed by recovery of a 0.2 kb fragment (fragment C) in the same manner as for fragment A.

Fragment A is a 817 bp long DNA fragment covering the region from the 300th C to the 1,116th C of the DNA fragment of SEQ ID NO: 1; fragment B is a 522 bp long DNA fragment covering the region from the 595th A to the 1,116th C of the DNA fragment of SEQ ID NO: 1; fragment C is a 200 bp long DNA fragment covering the region from the 917th G to the 1,116th C of the DNA fragment of SEQ ID NO: 1. Fragment A, B or C was ligated to the enhancer vector, previously digested with SmaI and BamHI, and introduced to *Escherichia coli* XL1-Blue. Plasmid DNA was extracted from the thus-obtained ampicillin-resistant strain, and cleaved with ScaI and HindIII; insertion of the desired fragment was confirmed. Specifically, it is expected that a 2.0 kb fragment will be found if fragment A is inserted, that a 1.7 kb fragment will be found if fragment B is inserted, and that a 1.4 kb fragment will be found if fragment C is inserted. pPG204-0.8 carrying fragment A, pPG204-0.5 carrying fragment B, and pPG204-0.2 carrying fragment C were thus obtained.

From *Escherichia coli* strains harboring pPG204-0.8, pPG204-0.5 and pPG204-0.2, respectively, plasmids were prepared by the cesium chloride equilibration density gradient centrifugation method in the same manner as in Example 1, followed by transfection of COS-1 cells. The luciferase activity of the extract from the transfected COS-1 cells was determined in the same manner as in Example 1, except that luminescence intensity was determined using a luminometer (LB 9501, produced by Belthold).

As a result, the smaller fragments were found to be 2 to 3 times more potent than the 1.1 kb SphI-NaeI fragment in terms of promoter activity.

Other modifications of the above described embodiments of the invention which are obvious to those skilled in the art are intended to be within the scope of the following claims.

| | Relative luminescence intensity (%) |
|---|---|
| pPG204-1.1 | 100 |
| pPG204-0.8 | 316 |
| pPG204-0.5 | 333 |
| pPG204-0.2 | 219 |

---

What is claimed is:

1. An isolated DNA having a sequence selected from the group consisting of:
    (a) a DNA sequence comprising a sequence of SEQ ID NO:1, or a fragment thereof;
    (b) a DNA sequence comprising a sequence of SEQ ID NO:2, or a fragment thereof;
    (c) a DNA sequence comprising a sequence of SEQ ID NO:3, or a fragment thereof;
    (d) a DNA sequence comprising a sequence of SEQ ID NO:4, or a fragment thereof; and
    (e) a DNA sequence capable of hybridizing to any one of (a) to (d) above at 65° C. for 20 hours in a solution containing 6×SSC, 1% sodium dodecyl sulfate, 100 µg/ml salmon sperm DNA and 5×Denhardt's,
wherein said isolated DNA has a promoter activity in an animal cell in vitro.

2. A recombinant DNA which comprises the isolated DNA of claim 1 and a useful gene operably linked thereto, wherein said useful gene encodes a protein expressible in an animal cell.

3. The recombinant DNA according to claim 2, wherein said useful gene is selected from the group consisting of a DNA encoding a protein, antisense DNA, antisense RNA, a polynucleotide encoding a decoy, and a ribozyme.

4. A vector which comprises the recombinant DNA of claim 2.

5. A vector which comprises the recombinant DNA of claim 3.

6. The vector according to claim 4, wherein the vector is a plasmid vector or a virus vector.

7. The vector according to claim 5, wherein the vector is a plasmid vector or a virus vector.

8. An in vitro animal cell wherein the recombinant DNA of claim 2 is introduced therein.

9. An in vitro animal cell wherein the recombinant DNA of claim 3 is introduced therein.

10. An in vitro animal cell transformed with the vector of claim 4.

11. An in vitro animal cell transformed with the vector of claim 5.

12. A method for producing a protein using an animal cell in vitro, comprising the steps of:
    (a) ligating a DNA encoding a desired protein downstream of the isolated DNA of claim 1 to obtain a recombinant DNA fragment in a manner such that the DNA encoding the desired protein can be expressed;
    (b) inserting the recombinant DNA fragment into a vector;
    (c) transforming an animal cell with the vector;
    (d) culturing the animal cell; and (e) recovering the desired protein from the culture.

13. A method for expressing a useful gene comprising the steps of:
   (a) ligating the useful gene downstream of the isolated DNA of claim 1 to obtain a recombinant DNA fragment in a manner such that the useful gene can be expressed and wherein said useful gene encodes a protein expressible in an animal cell;
   (b) introducing the recombinant DNA fragment into an animal cell in vitro; and
   (c) culturing the animal cell.

14. A method for expressing a useful gene comprising the steps of:
   (a) ligating the useful gene downstream of the isolated DNA of claim 1 to obtain a recombinant DNA fragment in a manner such that the useful gene can be expressed and wherein said useful gene encodes a protein expressible in an animal cell;
   (b) introducing the recombinant DNA fragment into a vector;
   (c) transforming an animal cell in vitro with the vector; and
   (d) culturing the animal cell.

* * * * *